United States Patent
Morris et al.

(10) Patent No.: US 8,728,562 B2
(45) Date of Patent: May 20, 2014

(54) IMPLANTABLE LEADS WITH A UNITARY SILICONE COMPONENT

(75) Inventors: Kimberly A. Morris, Minneapolis, MN (US); Andrew De Kock, Andover, MN (US); David A. Durand, Osceola, WI (US); Joshua Haarer, Hugo, MN (US); Ronald W. Kunkel, Jim Falls, WI (US); Peter J. Wolf, Dresser, WI (US); Joel T. Eggert, Champlin, MN (US); Joseph A. Cihlar, Glenwood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 431 days.

(21) Appl. No.: 12/949,638

(22) Filed: Nov. 18, 2010

(65) Prior Publication Data

US 2011/0156306 A1 Jun. 30, 2011

Related U.S. Application Data

(60) Provisional application No. 61/291,192, filed on Dec. 30, 2009.

(51) Int. Cl.
- *A61B 5/00* (2006.01)
- *A61N 1/00* (2006.01)
- *B05D 3/00* (2006.01)
- *B29C 45/14* (2006.01)

(52) U.S. Cl.
USPC ............ 427/2.1; 607/119; 607/122; 600/374; 600/486; 264/272.14; 29/846; 29/527.2

(58) Field of Classification Search
USPC ............ 427/2.1; 600/374, 486; 607/119, 112; 264/272.14; 29/846, 527.2
See application file for complete search history.

(56) References Cited

U.S. PATENT DOCUMENTS

| | | | |
|---|---|---|---|
| 4,962,767 | A | 10/1990 | Brownlee |
| 4,972,847 | A | 11/1990 | Dutcher et al. |
| 4,979,517 | A | 12/1990 | Grossman et al. |
| 5,042,463 | A | 8/1991 | Lekholm |

(Continued)

FOREIGN PATENT DOCUMENTS

| WO | WO9829055 A2 | 7/1998 |
|---|---|---|
| WO | WO0009178 A1 | 2/2000 |
| WO | WO2007001218 A1 | 1/2007 |
| WO | WO2007115198 A2 | 10/2007 |

OTHER PUBLICATIONS

Anderson, Sara E. et al., "Microanatomy of Human Left Ventricular Coronary Veins", The Anatomical Record, vol. 292, pp. 23-28, 2009.

(Continued)

*Primary Examiner* — Dah-Wei D Yuan
*Assistant Examiner* — Diane Zhang
(74) *Attorney, Agent, or Firm* — Faegre Baker Daniels LLP (57) ABSTRACT

A method of manufacturing a medical electrical lead includes molding a lead body pre-form, stringing an electrode onto the pre-form and overmolding the pre-form with a polymer to form a lead body portion. The pre-form has a proximal end, a distal end and at least one lumen extending between the proximal and distal ends. At least one asymmetric region of the pre-form has a transverse cross-section that has a non-circular outer dimension. The overmolding causes the asymmetric region to become substantially circular.

11 Claims, 8 Drawing Sheets

(56) References Cited

U.S. PATENT DOCUMENTS

| | | |
|---|---|---|
| 5,578,067 A | 11/1996 | Ekwall et al. |
| 6,119,044 A | 9/2000 | Kuzma |
| 6,240,322 B1 | 5/2001 | Peterfeso et al. |
| 6,430,425 B1 | 8/2002 | Bisping |
| 8,463,398 B2 | 6/2013 | Jackson et al. |
| 2003/0139794 A1 | 7/2003 | Jenney et al. |
| 2005/0049665 A1 | 3/2005 | Brabec et al. |
| 2005/0060885 A1* | 3/2005 | Johnson et al. .............. 29/846 |
| 2005/0182464 A1 | 8/2005 | Schulte et al. |
| 2005/0222660 A1 | 10/2005 | McAuliffe et al. |
| 2006/0009829 A1* | 1/2006 | Aron et al. .................. 607/122 |
| 2006/0121080 A1 | 6/2006 | Lye et al. |
| 2006/0122681 A1 | 6/2006 | Kroll et al. |
| 2007/0067008 A1 | 3/2007 | Scheiner et al. |
| 2007/0142890 A1* | 6/2007 | Zarembo et al. .............. 607/119 |
| 2008/0057784 A1 | 3/2008 | Zarembo et al. |
| 2009/0248126 A1* | 10/2009 | Nippoldt et al. .............. 607/119 |
| 2011/0160821 A1 | 6/2011 | Jackson et al. |
| 2011/0160822 A1 | 6/2011 | Jackson et al. |
| 2011/0160823 A1 | 6/2011 | De Kock et al. |

OTHER PUBLICATIONS

International Search Report and Written Opinion issued in PCT/US2010/058722, mailed Mar. 11, 2011.

United States Statutory Invention Registration No. H1905, to Michael R. S. Hill, published Oct. 3, 2000.

International Search Report and Written Opinion issued in PCT/US2010/058982, mailed Mar. 3, 2011, 12 pages.

\* cited by examiner

IMPLANTABLE LEADS WITH A UNITARY SILICONE COMPONENT

CROSS REFERENCE TO RELATED APPLICATION

This application claims the benefit of U.S. Provisional Application having Ser. No. 61/291,192, filed Dec. 30, 2009, entitled "IMPLANTABLE LEADS WITH A UNITARY SILICONE COMPONENT," which is incorporated herein by reference in its entirety.

TECHNICAL FIELD

The present invention relates to methods of manufacturing medical electrical leads. In particular, the invention relates to a method of manufacturing medical electrical leads that facilitates stringing conductors into and electrodes onto the medical electrical leads.

BACKGROUND

It is generally known to include a silicone component at a distal end of a medical electrical lead. The distal silicone component is designed to easily track through a guide catheter or other delivery system, to insulate conductors from one another and from the environment, and to help mitigate corrosion of the conductors. Conventional initial distal silicone designs have been formed using as much silicone as possible. One result of forming the distal silicone component in this manner is that if the outer diameter of the molded silicone part is much larger than the inner diameter of the electrodes to be strung onto the lead, dimensional interference between the internal features of the electrodes and the outer diameter of the lead formed by the silicone can occur. In these cases, in order to string the electrodes onto the lead, the molded silicone is compressed and/or stretched while the electrodes are slid over the silicone into their final positions.

SUMMARY

In Example 1, a method of manufacturing a medical electrical lead includes molding a lead body pre-form, stringing an electrode onto the pre-form and overmolding the pre-form with a polymer to form a lead body portion. The pre-form has a proximal end, a distal end and at least one lumen extending between the proximal and distal ends. At least one asymmetric region of the pre-form has a transverse cross-section that has a non-circular outer dimension. The overmolding causes the asymmetric region to become substantially circular.

In Example 2, the method according to Example 1, wherein molding the pre-form comprises forming an eccentric lumen within the pre-form.

In Example 3, the method according to Example 1 or 2, wherein molding the pre-form comprises forming at least one trough within the pre-form at the asymmetric region.

In Example 4, the method according to Examples 1-3, wherein molding the pre-form comprises forming a plurality of protrusions along a length of the pre-form.

In Example 5, the method according to Examples 1-4, wherein at least some of the protrusions extend radially outward to a length substantially equal to an outer diameter of the lead body.

In Example 6, the method according to Examples 1-5, wherein at least some of the protrusions extend radially outward beyond an outer diameter of the lead body.

In Example 7, a method of manufacturing a multi-lumen lead includes providing a pre-molded base of at least a portion of a lead body, stringing a plurality of electrodes over the pre-molded base and depositing a polymer onto the pre-molded base to form a lead body having a substantially smooth outer diameter. An outer diameter of the pre-molded base varies along a length of the pre-molded base.

In Example 8, the method according to Example 7, wherein the pre-molded base comprises at least one trough within the pre-molded base.

In Example 9, the method according to Examples 7 or 8, wherein the pre-molded base comprises as many troughs as electrodes.

In Example 10, the method according to Examples 7-9, wherein the pre-molded base comprises a plurality of protrusions along a length of the pre-molded base.

In Example 11, the method according to Examples 7-10, wherein at least some of the protrusions extend radially outward to a length substantially equal to an outermost diameter of the lead body.

In Example 12, the method according to Examples 7-11, wherein at least some of the protrusions extend radially outward beyond an outermost diameter of the lead body.

In Example 13, the method according to Examples 7-12, wherein depositing the polymer onto the pre-molded base comprises depositing liquid silicone rubber onto the pre-molded base.

In Example 14, a method of stringing an electrode onto a multi-lumen lead includes providing a pre-form of at least a portion of a distal portion of a lead body, positioning a plurality of electrodes along a length of the distal portion of the pre-form and depositing a layer of silicone over the pre-form.

In Example 15, the method according to Example 14, wherein the pre-form comprises at least one trough within the pre-form.

In Example 16, the method according to Examples 14 or 15, wherein the pre-form comprises three troughs of different sizes.

In Example 17, the method according to Examples 14-16, wherein the pre-form comprises a plurality of protrusions along a length of the pre-form.

In Example 18, the method according to Examples 14-17, wherein at least some of the protrusions extend radially outward to a length substantially equal to an outer diameter of the lead body.

In Example 19, the method according to Examples 14-18, wherein at least some of the protrusions extend radially outward beyond an outermost diameter of the lead body.

In Example 20, the method according to Examples 14-19, wherein the pre-form comprises a transition from polyurethane to silicone.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
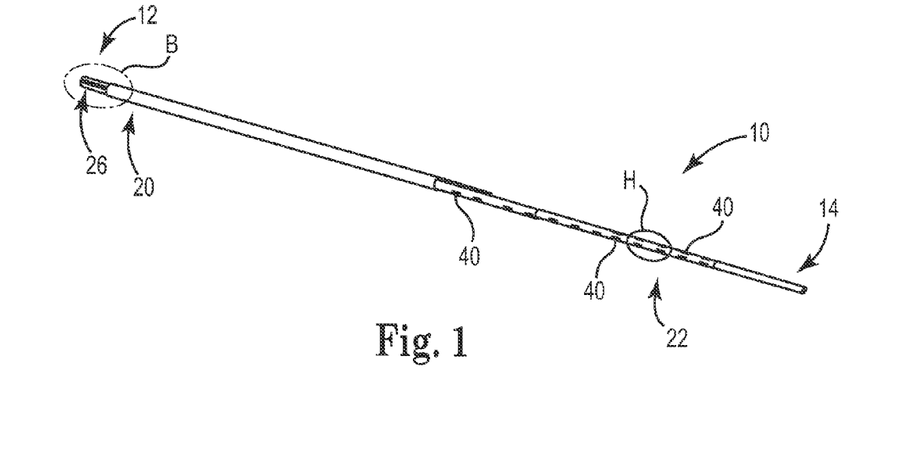
FIG. 1 is a perspective view of a pre-form that can be used in relation to embodiments of the present invention.
Figure 2:
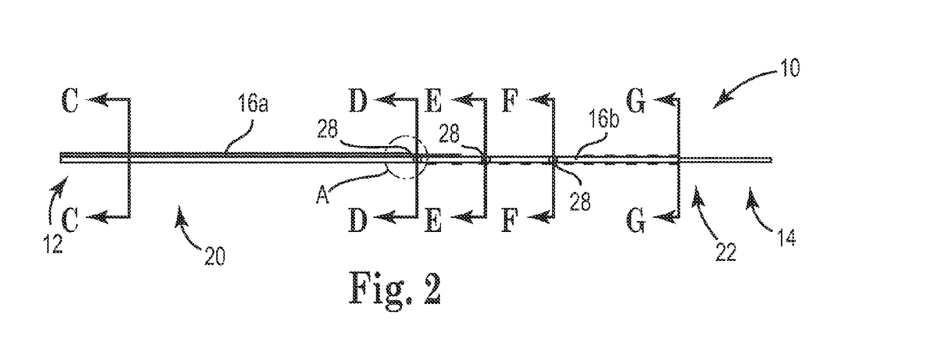
FIG. 2 is a cross-sectional side view of the pre-form that can be used in relation to embodiments of the present invention.

FIGS. 1 and 2 show a perspective view and a cross-sectional side view, respectively, of a lead body pre-form 10, or pre-molded base, of the present invention. The pre-form 10 forms a portion of a multi-lumen medical electrical lead. The lead includes a lead body, a coil conductor, a plurality of wire conductors and a plurality of electrodes. The lead body is a flexible tubular body including a proximal end and a distal end and defines a coil conductor lumen and a plurality of wire conductor lumens extending between the proximal and distal ends. The lead body can be made from any flexible, biocompatible material suitable for lead construction. In various embodiments, the lead is made from a flexible, electrically insulative material. In one embodiment, the proximal portion of the lead body is formed of polyurethane, for example, and the distal portion of the lead body is formed using the pre-form 10, and generally is formed of silicone, for example. In various embodiments, respective segments of the lead body are made from different materials, so as to tailor the lead body characteristics to its intended clinical and operating environments.

The pre-form 10 of the present invention includes particular design features that facilitate manufacturability of the lead body. In one embodiment, the pre-form 10 is formed of silicone. An example of a suitable silicone is liquid silicone rubber (LSR), although other materials are also contemplated. Exemplary design features include an eccentric coil conductor lumen between the proximal portion and the distal portion of the pre-form 10 that increases a nominal wall thickness between the coil conductor and the environment in the distal portion, a transition area of polyurethane and silicone in the proximal portion of the pre-form that contains and protects the conductors, trough designs to facilitate stringing of the electrodes onto the pre-form 10, and projections extending to or beyond the outer diameter of the lead body in order to prevent movement of the pre-form 10 during overmolding.

FIGS. 1 and 2 show the pre-form 10 prior to attachment to a lead body and prior to being overmolded. The pre-form 10 includes a proximal end 12, and a distal end 14. The pre-form also has an outer diameter (OD) that varies from the proximal end 12 to the distal end 14 of the pre-form 10. The outer diameter generally decreases in diameter from the proximal end 12 to the distal end 14, and the outer diameter may be stepped-down, or reduced in increments, at locations along the length of the pre-form 10. Both the size and shape of the outer diameter may vary from the proximal end 12 to the distal end 14. These variations allow electrodes to be slid proximally onto the pre-form 10 from the distal end 14 to different locations along the length of the pre-form 10 during manufacture of the lead with reduced deformation of the silicone of the pre-form 10. The shape of the outer diameter of pre-form 10 may be circular or non-circular depending upon the particular location along the length of the pre-form 10. At least one asymmetric region of the pre-form 10 has a transverse cross-section that has a non-circular outer dimension.

In one embodiment, the pre-form 10 is about 4 inches (10.16 centimeters (cm)) in length. The length of the pre-form is dependent upon the distance that electrodes are desired to be located from the distal end of the lead. Lengths other than 4 inches (10.16 cm) are, therefore, also contemplated.

The pre-form 10, as shown, also includes a coil conductor lumen 16, a first wire conductor lumen 18a, a second wire conductor lumen 18b and a third wire conductor lumen 18c (the wire conductor lumens 18a-18c are referred to collectively as "wire conductor lumens 18") for housing conductors. A first portion of the coil conductor lumen 16a extends through a proximal portion 20 of the pre-form 10 and a second portion of the coil conductor lumen 16b extends through a distal portion 22 of the pre-form 10. In one embodiment, the first portion of the coil conductor lumen 16a has a diameter of about 0.035 inches (0.889 millimeters (mm)) and the second portion of the coil conductor lumen 16b has a diameter of about 0.028 inches (0.711 mm). The dual portion coil conductor lumen 16 shown may accommodate a coil conductor that steps down or reduces its diameter along its length. Other coil conductors that do not include such a step-down may also be housed in the pre-form 10 described herein. Other configurations of the coil conductor lumen are, however, also contemplated (e.g., a coil conductor lumen having one diameter or more than two different diameters along its length).

Although the pre-form 10 is discussed and depicted in the figures as including three wire conductor lumens, the pre-form 10 may include any number of wire conductor lumens without departing from the intended scope of the present invention. In one embodiment, each of the wire conductor lumens 18a-18c has a diameter of about 0.0105 inches (0.267 mm).

Figure 3:
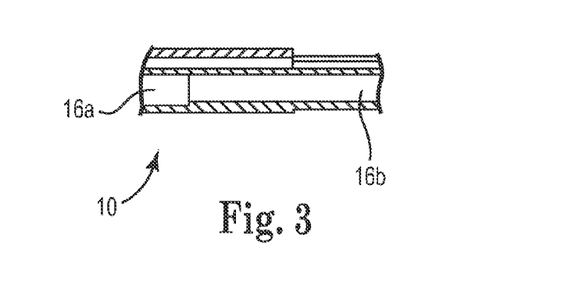
FIG. 3 is an enlarged side view of the pre-form of FIG. 2 at A.

FIG. 3 shows an enlarged view of a section of the pre-form 10 shown at A in FIG. 2. As can be seen in FIG. 3, the first and second portions 16a and 16b of the coil conductor lumen 16 in the proximal and distal portions 20 and 22 of the pre-form 10, respectively, are eccentric with respect to one another. Eccentric means that two lumens, for example, do not have the same center, and instead the lumen centers are set off from each other. The eccentric coil conductor lumens 16a and 16b allow for maintenance of a specific outer diameter, a minimum web thickness between the conductors and a minimum wall thickness between the conductors and the environment. In particular, the eccentric conductor coil lumen design allows the outer diameter of the pre-form 10, and the outer diameter of the resulting lead body, to stay small while increasing the width of the nominal wall between the coil conductor lumen 16 and the outer diameter. In one embodiment, the nominal wall increases by about 0.004 inches (0.102 mm) when the coil conductor lumens 16a and 16b are eccentric, rather than concentric.

One of the functions of the pre-form 10 is to electrically isolate the conductors and to allow translation of the conductors. The additional insulation gained from the eccentric coil conductor lumen design helps maintain electrical isolation between the conductors. The minimum wall thickness between the conductor lumens 16 and 18 and the outer diameter is such that there is a sufficient amount of silicone to electrically isolate the conductors. In one embodiment, the pre-form 10 has a minimum wall thickness of about 0.004 inches (0.102 mm). In addition, the increased thickness of the wall between the coil conductor lumen 16 and the environment makes the lead body more robust long term. The increased wall width also makes the lead body less prone to damage during subsequent manufacturing processes, such as stringing the conductors and electrodes onto the pre-form 10.

Figure 4A:
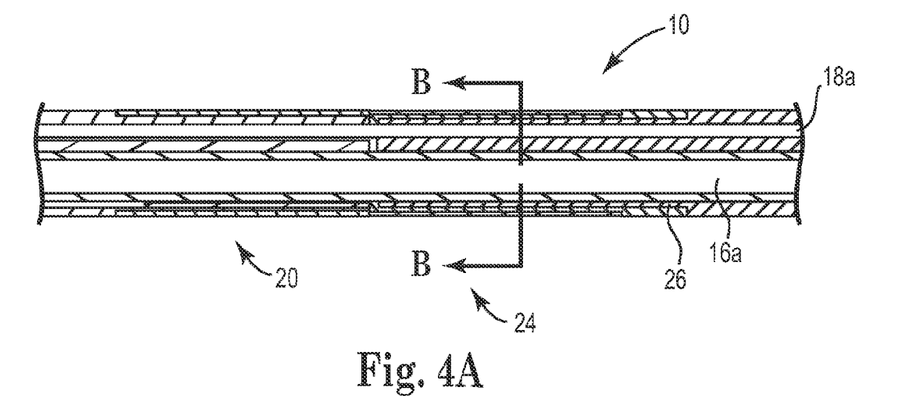
FIG. 4A is a cross-sectional side view of the pre-form at an area of transition from a proximal portion to a distal portion of the lead body.
Figure 4B:
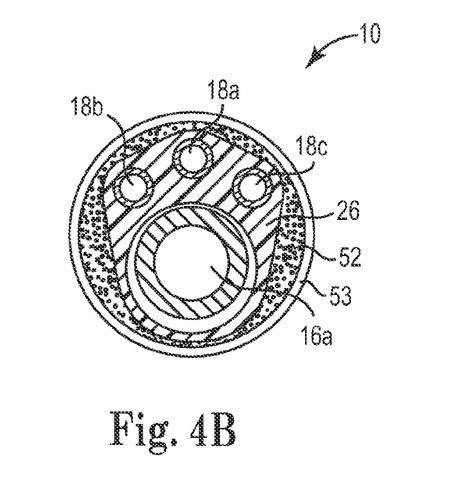
FIG. 4B is a cross-sectional view of the pre-form at line B-B of FIG. 4A.

FIG. 4A shows a cross-sectional side view of the pre-form 10 at an area of transition 24 of the pre-form 10, shown in FIG. 1 at B. FIG. 4B shows a cross-sectional view of the pre-form 10 at line B-B, shown in FIG. 4A. The transition area 24 is located at the proximal end 12 of the pre-form 10 near the transition between the proximal portion and the distal portion of the lead body. The proximal portion and the distal portion of the lead body are formed separately and are formed of different materials. For example, the proximal portion of the lead body is extruded and formed of polyurethane while the distal portion of the lead body is formed using the method of the present invention and is formed of silicone. In an embodiment, the silicone is a liquid silicone rubber (LSR). The pre-form 10 of the present invention thus includes a transition area 24 formed of polyurethane 53 (an outer layer) and silicone (which forms a multi-lumen tab 26 that is discussed below), with an adhesive 52 located in between the polyurethane and silicone, at or near the proximal end 12 of the pre-form (as shown in FIG. 1) between the proximal portion and the distal portion of the lead body to provide the conductors as the material of the lead body transitions. The transition area 24 contains and protects the conductors and the coil conductor lumen 16a within the lead body and from the environment.

To form the transition area 24, a multi-lumen tab 26 is preformed into the proximal portion 20 of the pre-form 10 and the polyurethane and silicone are joined using a fixtured region bond fill. The presence of the silicone around the coil conductor lumen 16a and between the coil conductor lumen 16a and the wire conductor lumens 18a-c within the pre-form 10 aids in flex fatigue robustness. As can be seen in FIG. 4B, silicone 26 is present around the entire coil conductor lumen 16 at the proximal portion 20 of the pre-form 10 and around all of the wire conductor lumens 18a-c.

Figure 5:
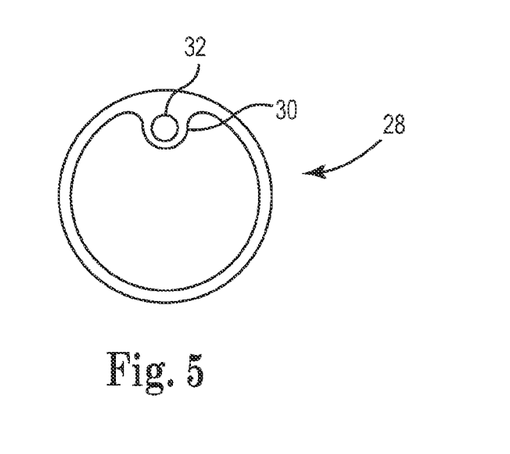
FIG. 5 is a front view of an electrode of the multi-lumen medical electrical lead.

FIG. 5 shows a front view of an electrode 28 of a multi-lumen medical electrical lead resulting from the pre-form 10 of the present invention. The electrode 28 is a ring or ring-like electrode that provides an exposed electrically conductive surface around all, or at least part of, the circumference of the lead body into which it is included. Generally, the electrode 28 has an inner diameter, an outer diameter and a protrusion 30 extending from the inner diameter. A lumen 32 extends through the protrusion 30 and is sized to allow a wire conductor to pass therethrough. In one embodiment, the multi-lumen medical electrical lead includes three electrodes, although other numbers of electrodes are also contemplated. In one embodiment, each electrode 28 has an inner diameter of about 0.059 inches (1.50 mm).

Figure 6A:
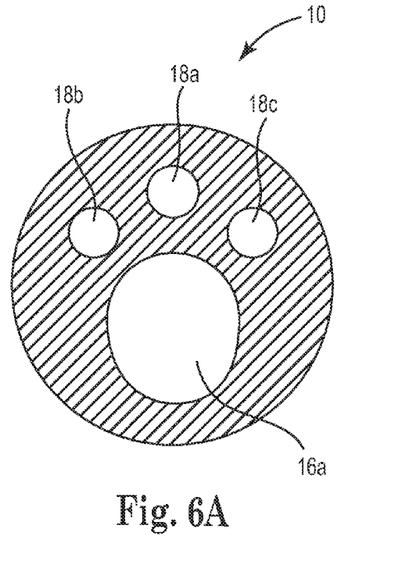
FIG. 6A is a cross-sectional area of the pre-form along line C-C of FIG. 2.

FIG. 6A shows a cross-sectional view of the pre-form 10 at line C-C shown in FIG. 2, proximal of the electrodes 28. At line C-C, the pre-form 10 has a circular shape and includes the coil conductor lumen 16a, the first wire conductor lumen 18a, the second wire conductor lumen 18b and the third wire conductor lumen 18c. As can be seen in FIG. 6A, the wire conductor lumens 18 are positioned above the coil conductor lumen 16 of the pre-form 10. However, other configurations of the conductor lumens are also contemplated. In the cross-section of the one embodiment shown, silicone comprises the cross-section, with the exception of voids forming the conductor lumens 16, 18.

In practice, a first electrode 28, as shown in FIG. 5, is strung over the pre-form 10 such that the lumen 32 in the protrusion 30 of the first electrode 28 lines up with the first wire conductor lumen 18a. Similarly, second and third electrodes 28 are strung onto the pre-form 10 proximal to the first electrode such that the lumen 32 in the protrusion 30 of each respective electrode is aligned with the second and third wire conductor lumens 18b and 18c, respectively.

Figure 6B:
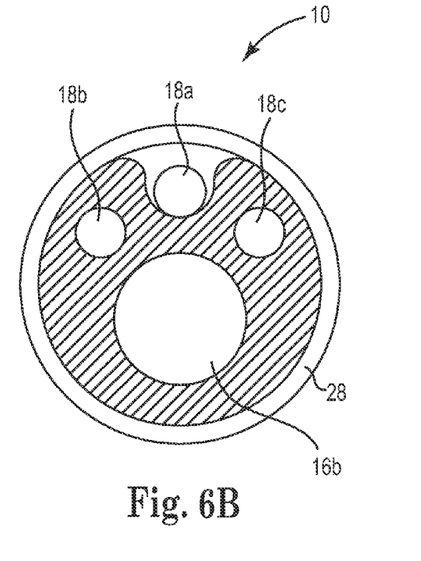
FIG. 6B is a cross-sectional area of the pre-form along line D-D of FIG. 2.
Figures 6C, 6D:
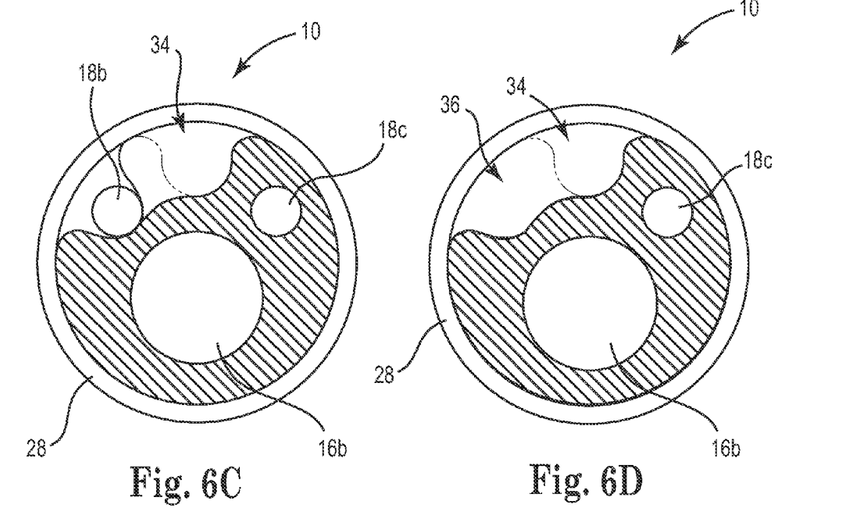
FIG. 6C is a cross-sectional area of the pre-form along line E-E of FIG. 2.
FIG. 6D is a cross-sectional area of the pre-form along line F-F of FIG. 2.

FIGS. 6B, 6C and 6D show cross-sectional views of the pre-form 10 at lines D-D, E-E and F-F shown in FIG. 2, respectively. FIG. 6B shows a cross-section of the pre-form 10 at the location of the first electrode 28, which is the closest electrode 28 to the proximal end 12 of the pre-form 10. Distal to line D-D, a first trough 34 (as shown in FIG. 6C) is carved out from, results or appears in the periphery of the circular shape of the pre-form 10 that exists proximal to line D-D. The first trough 34 (see FIG. 6C) defines an area matching or accounting for an area covered by the first wire conductor lumen 18a. The coil conductor lumen 16 and the second and third wire conductor lumens 18b and 18c are still defined within a periphery of the pre-form 10. The first trough 34 (see FIG. 6C) allows the first electrode 28 to slide along the pre-form 10 into position, at D-D, without the protrusion 30 of the first electrode 28 substantially deforming or compressing the pre-form 10. Because the electrodes 28 and wire conductors are strung from the distal end 14 of the pre-form 10 towards the proximal end 12 of the pre-form 10, the pre-form 10 at line D-D only needs to include one trough. The first electrode 28 is strung onto the pre-form 10 such that the protrusion 30 of the first electrode 28 lines up with the first trough 34 (see FIG. 6C). In this position, the lumen 32 in the protrusion 30 of the first electrode 28 is co-linear with the first wire conductor lumen 18a of the pre-form 10.

FIG. 6C shows a cross-section of the pre-form 10 at the location of the second electrode 28 along the pre-form 10. At line E-E, the pre-form 10 includes both the first trough 34 and a second trough 36 (with trough 36 shown in FIG. 6D). The second trough 36 (see FIG. 6D) is shaped to match or account for the area covered by the second wire conductor lumen 18b. The coil conductor lumen 16 and third wire conductor lumen 18c are still defined within a periphery of the pre-form 10 that exists at or proximal to line E-E. Because the second electrode 28 is positioned more distally along the pre-form 10 than the first electrode 28 and because the electrodes 28 and wire conductors are strung from the distal end 14 of the pre-form 10 towards the proximal end 12 of the pre-form 10, the pre-form 10 distal to line E-E includes less material than the pre-form 10 between line D-D and line E-E. The second trough 36 (in FIG. 6D) allows the second electrode 28 to be positioned on the pre-form 10 at E-E such that the lumen 32 within the protrusion 30 of the second electrode 28 is co-linear with the second wire conductor lumen 18b of the pre-form 10. In the embodiment shown, first wire conductor lumen 18a does not extend distally to be present at line E-E. The first wire conductor lumen 18a shown terminates at or just distal to the location of the first electrode 28.

FIG. 6D shows a cross-section of the pre-form 10 at the location of the third electrode 28 along the pre-form 10. At line F-F, the pre-form 10 includes the first trough 34, the second trough 36, and a third trough 38 (with trough 38 shown in FIG. 6E using dotted lines). The third trough 38 (see FIG. 6E) is shaped to match or correspond to the area covered by the third wire conductor lumen 18c and also extends around the remainder of the entire coil conductor lumen 16 that is not accounted for by the first and second troughs 34, 36. Because the third electrode 28 is positioned more distally along the pre-form 10 than the first two electrodes 28 and because the electrodes 28 and wire conductors are strung from the distal end 14 of the pre-form 10 towards the proximal end 12 of the pre-form 10, the pre-form 10 distal to line F-F includes less material than the pre-form 10 between line E-E and line F-F. The third trough 38 (see FIG. 6E) allows the third electrode 28 to be positioned on the pre-form 10 at F-F such that the lumen 32 within the protrusion 30 of the third electrode 28 is co-linear with the third wire conductor lumen 18c of the pre-form 10. In the embodiment shown, second wire conductor lumen 18b does not extend distally to be present at line F-F. The second wire conductor lumen 18b shown terminates at or just distal to the location of the second electrode 28.

Figure 6E:
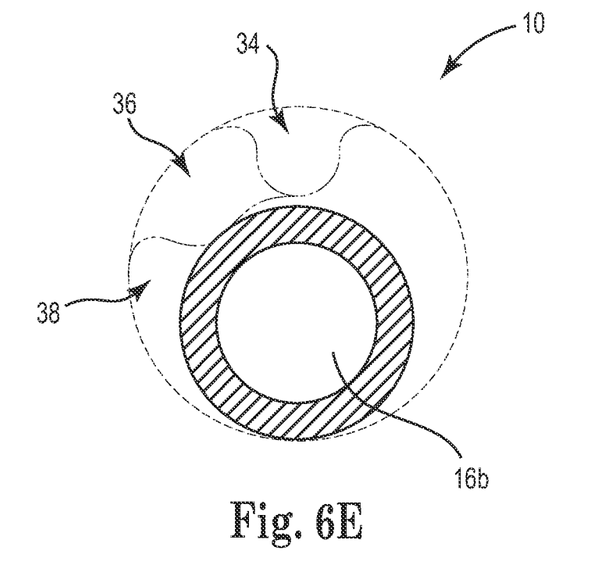
FIG. 6E is a cross-sectional area of the pre-form along line G-G of FIG. 2.

FIG. 6E shows a cross-section of the pre-form 10 distal to the location of the third electrode 28 along the pre-form 10. At line G-G, the pre-form 10 has a generally circular shape and only defines the coil conductor lumen 16. In the embodiment shown, third wire conductor lumen 18c does not extend distally to be present at line G-G. The third wire conductor lumen 18c terminates at or just distal to the location of the third electrode 28. The first trough 34, the second trough 36 and the third trough 38 are all shown using dotted lines in FIG. 6E for illustrative purposes only. The area of all three troughs actually is a void space around the pre-form 10 remaining, which defines a circular-shaped portion of silicone forming or surrounding coil conductor lumen 16b.

As can be seen in FIGS. 6A-6E, the pre-form 10 includes the most material at line C-C, the cross-section closest to the proximal end 12 of the pre-form 10 and proximal of any electrodes 28. Travelling from the proximal end 12 to the distal end 14 of the pre-form 10, additional silicone is removed or absent from the outer diameter of the pre-form 10 at each electrode location (and distal to that electrode location) such that the outer diameter of the pre-form 10 may be non-circular. The material of the pre-form 10 decreases from the proximal end 12 to the distal end 14 of the pre-form 10 such that the distal end 14 of the pre-form 10 at line G-G is shaped like a hollow circle having a smaller outer diameter than the outer diameter of the pre-form 10 at line C-C.

Once the electrodes 28 and conductors have been strung onto the pre-form 10, a polymer, such as liquid silicone rubber, is overmolded onto the pre-form 10 to form a lead body having a substantially circular outer diameter. Thus, the pre-form 10 includes a sufficient amount of insulation surrounding all of the conductor lumens 16 and 18, but with material removed along the length of the pre-form 10 to allow the electrodes 28 to slide into place without requiring any stretching or compressing of the pre-form 10. Referring back to FIG. 1, and as mentioned earlier, internal overmolding over the pre-form 10 can be used to position or maintain the electrodes 28 at the desired locations along the pre-form 10 and to also create the desired external geometry of the distal portion 22 of the lead body. Overmolding relies on using a polymer, such as liquid silicone rubber, in an injection molding press. This process subjects the pre-form 10 to both heat and pressure in order to cure the newly added polymer.

In order to overmold the pre-form, with associated electrodes, the pre-form with electrode is placed in a mold cavity. In one embodiment, the mold has an elongated, cylindrical shape. It is desired to center the pre-form 10 in the mold cavity in order to allow polymer to be injected around the pre-form 10 and between the pre-form 1 and an inner surface of the mold cavity. Centering the pre-form 10 allows production of a final lead body with a repeatable wall thickness and predictable coil conductor lumen location.

Figure 7:
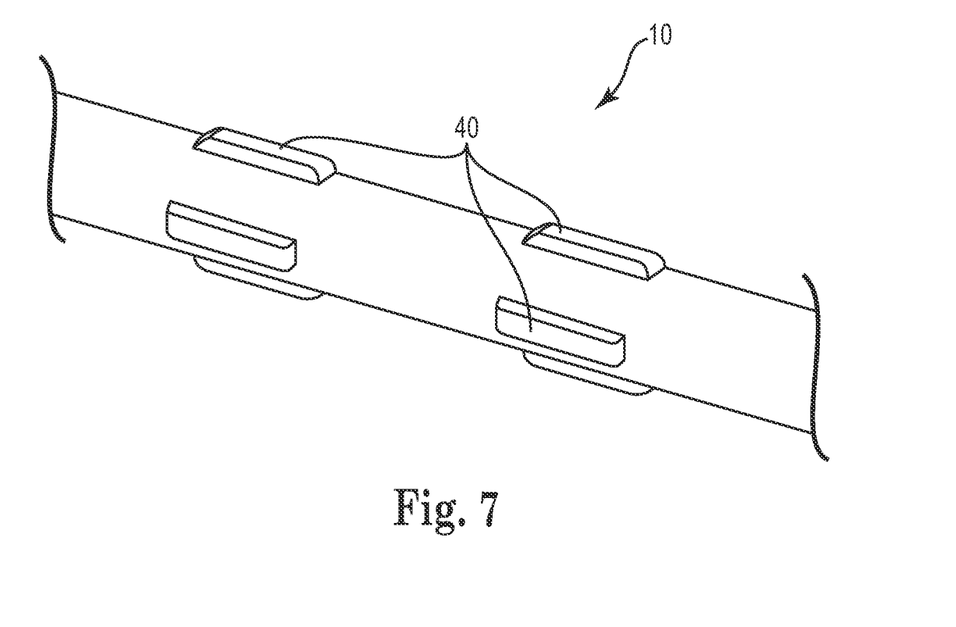
FIG. 7 is an enlarged view of the pre-form of FIG. 1 at H.

In order to center the pre-form, the pre-form 10 may include a plurality of protrusions 40 along part of the length of the pre-form 10 that contact the inner surface of the molding cavity and hold the pre-form 10 in the desired position in the mold cavity. One embodiment of protrusions are shown in FIG. 1 (40). A close-up view of protrusions 40 are shown in FIG. 7. The protrusions 40 are manufactured to have a diameter substantially equal to the outer diameter of the desired final lead body with the overmolding, or, in other words, a length that extends radially outward to the outermost diameter of the final lead body. The protrusions 40 are located around the diameter or outer circumferential surface of the pre-form 10 in such a way that they can be used to stabilize the pre-form 10 in the mold used for overmolding while not impeding the electrode stringing process. Protrusions 40 have a rectangular shape, and extend in a longitudinal direction along the pre-form 10. However, other shapes and configurations of protrusions 40 are also contemplated.

The protrusions 40 use compression (against the inner surface of the molding cavity) to keep the pre-form 10 centered. After the pre-form 10 is overmolded with silicone, the projections 40, which may also comprise the same silicone, may essentially disappear into the distal end portion of the lead.

Figure 8:
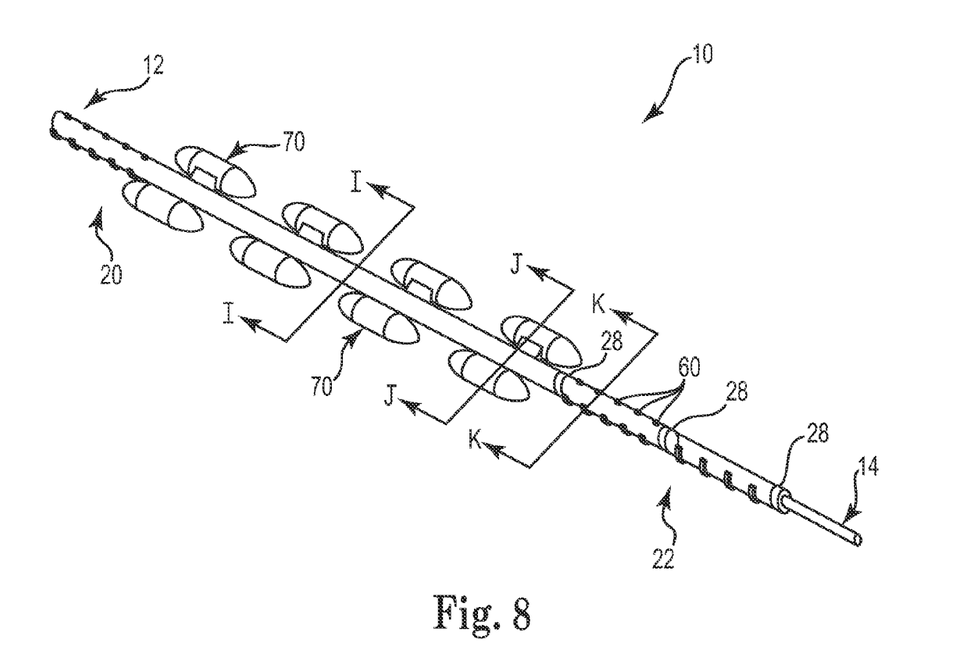
FIG. 8 is a perspective view of a pre-form that can be used in relation to embodiments of the invention.

FIG. 8 shows an embodiment of pre-form 10 that, instead of projections 40, includes centering nubs 60 and pill-shaped nubs 70 that are used to center the pre-form in a molding cavity in order to overmold the pre-form 10. The centering nubs 60 extend circumferentially around at least a portion of the pre-form 10. In other words, the centering nubs 60 extend radially outward from the pre-form 10. Like the projections 40, the centering nubs 60 use compression against the inner surface of the molding cavity in order to hold the pre-form 10 in place for overmolding. The centering nubs 60 may be used alone or in combination with pill-shaped nubs 70.

Rather than compression, the pill-shaped nubs 70 can use tension in order to hold the pre-form 10 in place in the molding cavity for overmolding. Pill-shaped nubs 70 can be attached or extended from the remainder of the pre-form 10 at spaced apart locations. The pill-shaped nubs 70 have a shape and size that is configured to correspond to a part (not shown) of the molding cavity that is adapted to retain or hold the pill-shaped nubs 70 in place.

During overmolding, the pill-shaped nubs 70 can be located outside of the molding cavity. The molding cavity used then would include openings through which at least a portion of the pill-shaped nubs 70 would extend. Alternatively, the molding cavity could be designed to otherwise retain the pill-shaped nubs 70. After overmolding, the pill-shaped nubs 70 are removed from the remainder of the lead body. The pill-shaped nubs 70 may be used alone or in combination with the centering nubs 60, for example.

Figure 9A:
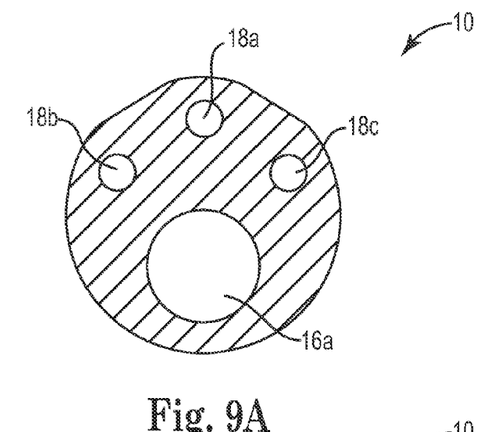
FIG. 9A is a cross-sectional view of the pre-form of FIG. 8 at line I-I.
Figure 9B:
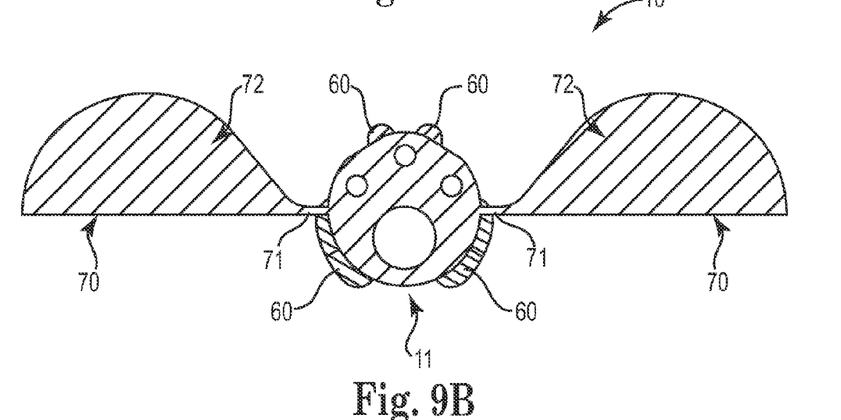
FIG. 9B is a cross-sectional view of the pre-form of FIG. 8 at line J-J.

FIG. 9A illustrates the cross-section of pre-form 10 at line I-I. The cross-sectional shape is generally the same as in FIG. 1 when projections 40 are used instead. FIG. 9B illustrates that the centering nubs 60 may be located at various locations around the periphery or circumferential surface of the nearly circular-shaped center portion of pre-form 10, and extend radially outward from the pre-form 10. The locations of the centering nubs 60 are chosen to allow electrodes 28 to be strung onto the pre-form 10 from the distal end.

FIG. 9B also shows one embodiment of the pill-shaped nubs 70 in cross-section. The pill-shaped nubs 70 are formed as part of the pre-form 10. In the embodiment shown, there is a connection area 71 that connects a pill-shaped portion 72 of the pill-shaped nub 70 to the central, generally circular-shaped portion 11 of the pre-form 10. After overmolding, the pill-shaped nubs 70 may be removed from the remainder of the lead body by disconnecting each connection area 71. The pill-shaped nubs 70 may also comprise silicone or other suitable materials that comprise the remainder of the pre-form 10.

Figure 9C:
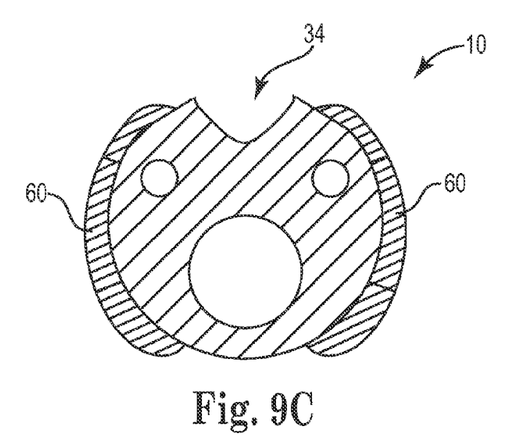
FIG. 9C is a cross-sectional view of the pre-form of FIG. 8 at line K-K.

FIG. 9C shows a cross-section of pre-form 10 at line K-K, which illustrates another embodiment of centering hubs 60 that may be used. In the embodiment shown, one electrode 28 may be placed on the pre-form proximal to the cross-section K-K. Thus, FIG. 9C includes a void portion, or trough, 34 in its circular cross-section to allow the electrode 28 to be strung from the distal end. Although not shown with additional cross-sectional views, the troughs 36, 38 illustrated in FIGS. 6C, 6D and 6E would also be present in order to string two additional electrodes 28 on pre-form 10 of FIG. 8.

During the overmolding process, the proximal portion of the lead body is also connected to the pre-form 10 to form the lead body. The overmolding causes the asymmetric region of the pre-form 10 to become substantially circular.

Figure 10:
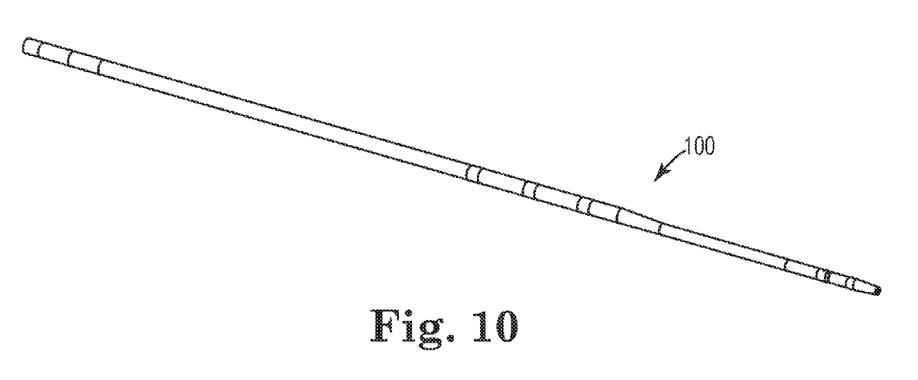
FIG. 10 is a perspective view of a multi-lumen medical electrical lead including the pre-form of the present invention.

FIG. 10 illustrates a fully assembled lead 100 that include pre-form 10 of the present invention. Pre-form 10 is not separately visible, preferably, once the pre-form 10 is overmolded in order to form lead 100.

The pre-molded base and method of manufacturing a lead of the present invention facilitates manufacturability of the lead. The pre-molded base, or pre-form, increases nominal wall thicknesses, facilitates stringing of electrodes onto the pre-molded base and prevents movement of the pre-molded base during overmolding.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of stringing an electrode onto a multi-lumen lead, the method comprising:

providing a polymeric pre-form, an outer profile of the pre-form varying along a longitudinal section of the pre-form such that a cross-sectional area of the pre-form decreases from a proximal end to a distal end of the pre-form, the cross-sectional area transverse of a longitudinal axis of the longitudinal section;

positioning a plurality of electrodes along the longitudinal section such that the plurality of electrodes are respectively positioned at a plurality of different locations along the longitudinal section, the cross-sectional area of the pre-form different at each of the plurality of different locations; and depositing a layer of silicone over the pre-form, the layer of silicone deposited by being overmolded around the pre-form, the layer of silicone defining an outer surface of a lead body.

2. The method of claim 1, wherein the pre-form comprises at least one trough within the pre-form.

3. The method of claim 2, wherein the pre-form comprises three troughs of different sizes.

4. The method of claim 1, wherein the pre-form comprises a plurality of protrusions along a length of the pre-form.

5. The method of claim 4, wherein at least some of the protrusions extend radially outward to a length equal to an outer diameter of the lead body.

6. The method of claim 4, wherein at least some of the protrusions extend radially outward beyond an outermost diameter of the lead body.

7. The method of claim 1, wherein the pre-form comprises a transition from polyurethane to silicone.

8. The method of claim 1, wherein the pre-form comprises at least one asymmetric region having a transverse cross-section that has a non-circular outer profile.

9. The method of claim 8, wherein depositing the layer of silicone comprises depositing the layer of silicone over the at least one asymmetric region such that the lead body is formed to be circular along the at least one asymmetric region of the pre-form.

10. The method of claim 1, wherein the pre-form comprises an eccentric lumen within the pre-form.

11. A method of forming a lead body, the method comprising:

providing a polymeric pre-molded base, an outer profile of the pre-molded base varying along a longitudinal section of the pre-molded base such that a cross-sectional area of the pre-molded base decreases from a proximal end to a distal end of the pre-molded base, the cross-sectional area transverse of a longitudinal axis of the longitudinal section;

positioning a plurality of electrodes along the longitudinal section such that the plurality of electrodes are respectively positioned at a plurality of different locations along the longitudinal section, the cross-sectional area of the pre-form different at each of the plurality of different locations; and depositing a layer of polymer on the pre-molded base to form an outer surface of the lead body, the polymer deposited by being overmolded around the pre-molded base.

* * * * *